United States Patent [19]

Harrel

[11] Patent Number: 5,378,150
[45] Date of Patent: Jan. 3, 1995

[54] METHODS AND APPARATUS FOR CONTROLLING THE AEROSOL ENVELOPE GENERATED BY ULTRASONIC DEVICES

[76] Inventor: Stephen K. Harrel, 4510 Ridge Rd., Dallas, Tex. 75229

[21] Appl. No.: 900,617

[22] Filed: Jun. 18, 1992

[51] Int. Cl.⁶ ............................................. A61C 17/06
[52] U.S. Cl. .................................... 433/91; 433/119; 604/22
[58] Field of Search ................... 433/28, 91, 119; 604/22

[56] References Cited

U.S. PATENT DOCUMENTS

| | | | |
|---|---|---|---|
| 2,246,916 | 6/1941 | Fischer | 77/55 |
| 3,126,889 | 3/1964 | Blumenfeld | 128/303 |
| 3,512,258 | 5/1970 | Johnson | . |
| 3,526,219 | 9/1970 | Balamuth | 433/119 X |
| 4,061,146 | 12/1977 | Baehr et al. | 128/305 |
| 4,111,208 | 9/1978 | Leuenberger | 128/305.1 |
| 4,176,453 | 12/1979 | Abbott | 433/82 |
| 4,253,831 | 3/1981 | Eaton, II | 433/91 |
| 4,428,748 | 1/1984 | Peyman et al. | 604/22 |
| 4,634,420 | 1/1987 | Spinosa et al. | 604/22 |
| 4,676,750 | 6/1987 | Mason | 433/101 |
| 4,692,139 | 9/1987 | Stiles | 604/22 |
| 4,692,140 | 9/1987 | Olson | 604/40 |
| 4,816,018 | 3/1989 | Parisi | 604/22 |
| 4,917,603 | 4/1990 | Haack | 433/29 |
| 4,921,375 | 5/1990 | Famulari | 408/67 |
| 4,964,849 | 10/1990 | Robicsek | 604/35 |
| 5,052,411 | 10/1991 | Schoolman | 128/863 |
| 5,122,153 | 6/1992 | Harrel | 606/180 |
| 5,123,903 | 6/1992 | Quaid et al. | 604/22 |
| 5,192,267 | 3/1993 | Shapiro et al. | 604/22 |

OTHER PUBLICATIONS

Instruction manual for Dentsply ® Bobcat ™ Ultrasonic Scaler, 1989.

*Primary Examiner*—Cary E. O'Connor
*Attorney, Agent, or Firm*—Richards, Medlock, & Andrews

[57] ABSTRACT

Disclosed is a suction hood assembly that is attachable to an ultrasonic handpiece, as well as to a source of suction. The suction hood assembly includes a portion thereof that opens in an area adjacent the ultrasonic tip to provide an area of influence of the suction and thereby recover microdroplets of body fluids, matter and water mist. The suction can be used to control the size of the aerosol envelope generated when the water stream from the ultrasonic device is directed toward the ultrasonic-moving tip. The size of the aerosol envelope can be substantially reduced to a small area of operation, thereby minimizing the dispersion of germs, viruses and body fluids from the patient to the surgeon. The suction tube assembly is easily attached or removed from the ultrasonic handpiece, is easily manufactured, cost effective and thus is disposable.

32 Claims, 3 Drawing Sheets

METHODS AND APPARATUS FOR CONTROLLING THE AEROSOL ENVELOPE GENERATED BY ULTRASONIC DEVICES

FIELD OF THE INVENTION

The present invention relates in general to medical and dental ultrasonic devices that generate an aerosol cloud or envelope, and more particularly to attachments utilized with ultrasonic devices for recovering the aerosol cloud generated thereby, and for controlling the size thereof.

BACKGROUND OF THE INVENTION

Ultrasonic devices are well known in the medical and dental field for use in tissue removal, or removal of organic and other types of deposits. When employed in the practice of periodontics, ultrasonic scalers are fitted with a pointed tip or end adapted for scraping calculus or tartar deposits. The ultrasonic vibrations of the tip facilitate the removal of such deposits on hard tissue, such as bone or teeth. In this type of application, the ultrasonic scaler includes a handpiece with a "pile" housed therein for generating the ultrasonic vibrations. A replaceable ultrasonic insert, fitted with the tip, is inserted into the end of the handpiece and connected to the pile for transferring the ultrasonic vibrations to the tip. A flow of water is also directed through the handpiece to cool the ultrasonic pile as it converts high frequency electrical energy to the mechanical vibrations. The water absorbs the heat generated by the pile, thereby maintaining the pile at an appropriate operating temperature. The water exits the insert via an orifice, is directed to the tip and, because of the ultrasonic vibrations of the tip, generates an aerosol cloud or mist. The water stream particles that are directed toward the tip, are broken into microdroplets which can create a large globe-shaped envelope, ranging in size up to 48 inches in diameter.

The aerosol cloud of microdroplets can also include small tissue fragments and droplets of body fluids, including blood, which become airborne and, unless specific precautions are taken by the surgeon or doctor, can be inhaled. It can be appreciated that various contagious viruses and other organisms can be transferred from the patient, via the aerosol cloud, to the surgeon. In addition, the aerosol cloud is disadvantageous for both the patient and the surgeon, in that after several minutes of utilization of the ultrasonic device, both the patient and the doctor can become wet or soaked.

Insofar as the water flow through the ultrasonic device is necessary for cooling, it cannot be interrupted during the operation of the device without overheating and potentially damaging the device. It is also believed that there may be a beneficial result of the ultrasonic water jet in the area of operation, as it is believed that the water jet provides cavitation for facilitating removal of stains and deposits.

Attempts have been made to control water jets in dental equipment, such as illustrated in U.S. Pat. No. 4,253,831 by Eaton, II. According to this patent, an aspirating dental device is fitted with a pliable sleeve over a contra-angle type of dental drill to form an airflow passage between the pliable sleeve and the handpiece itself. An airflow passage inlet exists near the working end of the dental handpiece, while a vacuum or suction is applied to the outlet end. It is believed that such a concept is inoperable as the sleeve must be somewhat pliable to be inserted on or removed from the irregular shaped dental device, and that being the case, the suction applied to the outlet end thereof would collapse the sleeve and interrupt or severely restrict the suction therethrough. The end result would be the inability to aspirate fluids at the working end of the device. Further, the pliable removable sleeve would be constricted around the dental device when the doctor grasps the device for use on a patient, thereby compromising the utility of the device. It should additionally be noted that the turbine exhaust of the Eaton, II air-driven dental drill is located within the airflow passage inlet. The high pressure exhaust from the dental drill will greatly reduce or nullify the low volume suction, and can result in no suction at all.

From the foregoing, it can be seen that a need exists for an improved mist or aerosol recovery device, usable with an ultrasonic scaler to reduce the spread of germs, viruses, and contaminated particles suspended in the cloud. A further need exists for a device that reduces the extent of the aerosol envelope, without reducing the cooling capability of the water stream. A related need exists for an attachment that reduces the amount of hot water that is dispensed from the ultrasonic device into the patient's mouth.

Yet another need exists for an aerosol recovery attachment that is removable from the conventional handpiece, is low cost, and thus is disposable for the surgeon.

SUMMARY OF THE INVENTION

The principles and concepts of the invention are disclosed for a technique and apparatus to reduce and control the aerosol envelope produced by water-cooled ultrasonic devices. According to the preferred embodiment of the invention, a suction hood assembly is attached to the handle of an ultrasonic handpiece, adjacent the end where the small water jet is directed to the ultrasonic tip held by the insert. By controlling the amount of suction in the annulus between the ultrasonic insert and the suction hood, the amount of water in the stream that reaches the ultrasonic tip can be controlled, thereby controlling the generation of water mist and thus the extent of the aerosol envelope. In addition, the suction produced at the end of the ultrasonic insert is also effective to recover substantial water mist from the envelope, thereby also controlling the size thereof. In view that the water flowing through the ultrasonic handle absorbs heat and cools the device, the control and recovery of a portion of the heated water stream that reaches the tip also results in a lower operating temperature of the ultrasonic tip. By reducing the amount of hot water that is dispensed in the mouth of the patient, discomfort to the patient is also reduced.

In accordance with one embodiment of the invention, the suction hood includes a cylinder body that is insertable onto the end of the ultrasonic handpiece into which the replaceable ultrasonic insert and tip are inserted for operation. One end of the cylinder body fits tightly to the ultrasonic handpiece for securing the hood to the device, while the other end of the cylinder is radially spaced about the insert to form an annulus. A suction tube is formed or attached into an opening in the sidewall of the cylinder body, and connected to a source of suction.

When the suction hood assembly is secured to the ultrasonic device and connected to a source of suction, a suction is developed in the annulus between the ultrasonic insert and the suction hood cylinder. The opening of the annulus is generally at the base of the ultrasonic tip, around the insert. The influence of the suction attracts a portion of the water stream from the jet, as well as a portion of the water mist of the envelope generated by the interaction of the ultrasonic vibrating tip and the water stream. By controlling the amount of suction to the suction hood assembly, the size of the envelope can be controlled.

Another advantage realized by the invention is that a portion of the heated water jetted from the ultrasonic device toward the tip is prevented from reaching the tip, thereby resulting in decreased temperatures of the ultrasonic tip. Another advantage realized by the invention is that by controlling the size of the water mist envelope, the area and volume of viruses, germs and bacteria suspended in the mist is reduced, thereby reducing the exposure of the doctor or surgeon to contagious or contaminating elements.

The principles and concepts of the invention can be embodied in other forms. For example, the cylinder body of the assembly can be made with different diameters, one diameter for fitting to the surgical handpiece, and another section having a different diameter to provide for a sufficient area of suction to recover and control the aerosol envelope.

In another embodiment, a plastic cylinder body can be elongated and extended around the handpiece of the ultrasonic assembly. In this embodiment, the extended portion of the plastic cylinder body is removable and thus sterilizable, and also functions to provide a thermal insulation between the surgeon's hand and the heat-generating ultrasonic pile housed within the ultrasonic handpiece.

In yet another embodiment, the suction hood assembly can be fabricated with the ultrasonic device, integral therewith. While cleaning or sterilization of this embodiment may be more difficult, the control of the aerosol envelope remains a decided advantage.

The ultrasonic device and attachment of the invention can be advantageously used in conjunction with an air suction/pressure control system. The control system includes a holder for removably holding or cradling the ultrasonic device. When the ultrasonic device is placed in the holder, a switch therein is effective to remove suction from the suction hood assembly and thereby stop the annoying suction hiss. The holder also removes air pressure and thus electrical power from the ultrasonic device during periods when it is held within the holder. On removal of the ultrasonic device from the holder, suction is applied to the suction hood assembly and electrical power is coupled to the ultrasonic device.

BRIEF DESCRIPTION OF THE DRAWINGS

Further features and advantages will become more apparent from the following and more particular description of the preferred embodiment of the invention, as illustrated in the accompanying drawings in which like reference characters generally refer to the same parts throughout the views, and in which.

DETAILED DESCRIPTION OF THE INVENTION

Figure 1:
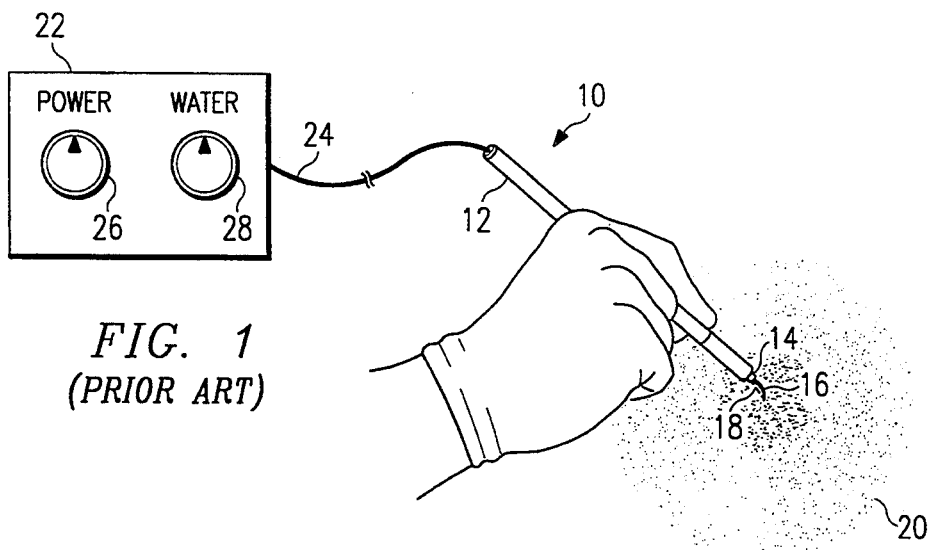
FIG. 1 illustrates a conventional ultrasonic device during operation, in which an aerosol cloud or envelope is generated.

FIG. 1 illustrates an ultrasonic handpiece assembly 10 of the type well known in the medical and dental fields. The assembly 10 includes a handpiece 12 and an interchangeable insert 14 with a tip 16. The tip 16 is made integral with the insert 14 so that tips having different angular orientations or tip edges can be utilized and interchangeably used with the same handpiece 12. The handpiece 12 includes an internal ultrasonic generator, or pile, providing high speed, microscopically small mechanical vibrations coupled to the insert 14, and therethrough to the tip 16. Vibrations up to 25,000 cycles per second are typically generated by the generator housed in the ultrasonic handpiece 12. The high frequency vibrations of the tip 16 are effective to dislodge calculus, tartar, deposits and stains from hard tissues, such as teeth and bones. There are many other applications for ultrasonic devices in the medical and dental fields.

Tap water is supplied to the handpiece 12 to cool the ultrasonic generator. The ultrasonic handpiece 12 is cooled by a water stream that absorbs heat from the handpiece 12, which water is then forced through a channel in the insert 14, out of an opening or orifice in the end thereof, and toward the tip 16. The water jet is shown in FIG. 1 as reference character 18. The water jet 18 hitting the vibrating tip generates a water mist cloud defining an aerosol envelope 20. Depending upon the flow rate of water forced through the handpiece assembly 10, the size of the aerosol envelope 20 can reach 2-3 feet, or more. In many instances, the water envelope gets both the surgeon and the patient wet, thereby resulting in an uncomfortable and undesirable environment. In addition, microdroplets of tissue and body fluids of the patient can become airborne in the envelope 20 and transferred to the surgeon via the aerosol envelope 20. It can be appreciated that when the ultrasonically vibrating tip 16 touches blood or saliva, such fluids are atomized, thereby causing microdroplets thereof to become airborne. In view of the possibility of the AIDS virus being transferred from the patient to the surgeon by way of the aerosol envelope 20, it is highly desirable to substantially control the size of the envelope and thus reduce or eliminate the transfer of matter between the patient and the surgeon via the aerosol envelope 20.

The ultrasonic handpiece assembly 10 is connected to a control unit 22 by way of a cable 24. The cable 24 includes one or more conductors for coupling high frequency electrical energy to the handpiece assembly 10, which then converts the electrical energy into corresponding mechanism vibrations. In addition, water is coupled under pressure by way of a conduit in the cable 24 to the handpiece assembly 10 for cooling thereof. Because of the substantial thermal energy generated by the conversion of electrical to mechanical energy in the handpiece assembly 10, such assembly must be cooled. Otherwise, the life of the assembly would be reduced, and the assembly would become too hot to handle by the surgeon. In addition, the water jet 18 co-acts with the ultrasonic vibrating tip 16 to result in what is believed to be a cavitation action that facilitates the cleaning or removal of matter from hard tissue. As will be described in more detail below, the tip 16 can reach a temperature of 140° F., which often becomes uncomfortable for the patient as the heat is transferred to the hard tissue.

The ultrasonic control unit 22 includes a manual control 26 for controlling the power coupled to the ultrasonic handpiece assembly 10. The power control 26 essentially varies the amplitude of the electrical energy which, when converted to mechanical energy, varies the amplitude of the mechanical vibrations of the tip 16. A water control 28 controls the pressure of water coupled to the handpiece assembly 10, and thus the amount of water forced through the assembly 10 and jetted to the tip 16. A recommended water flow through a conventionally available ultrasonic scaler is about 35 cc of water per minute to achieve adequate cooling. This flow rate is such that a patient must swallow or spit every 30–40 seconds. As can be appreciated, the greater the water flow through the handpiece assembly 10, the cooler the assembly will operate, as well as the tip 16. However, with a greater water flow, the size of the aerosol envelope 20 increases, thereby exacerbating the situation. Increasing the water flow will also increase the volume of hot water to the patient's mouth, thereby increasing discomfort to the patient. Ultrasonic equipment with which the invention is well adapted for use includes an ultrasonic scaler obtainable from Dentsply International, Inc., 570 West College Avenue, York, Pa., and known by the trademark "BOBCAT".

Figure 2:
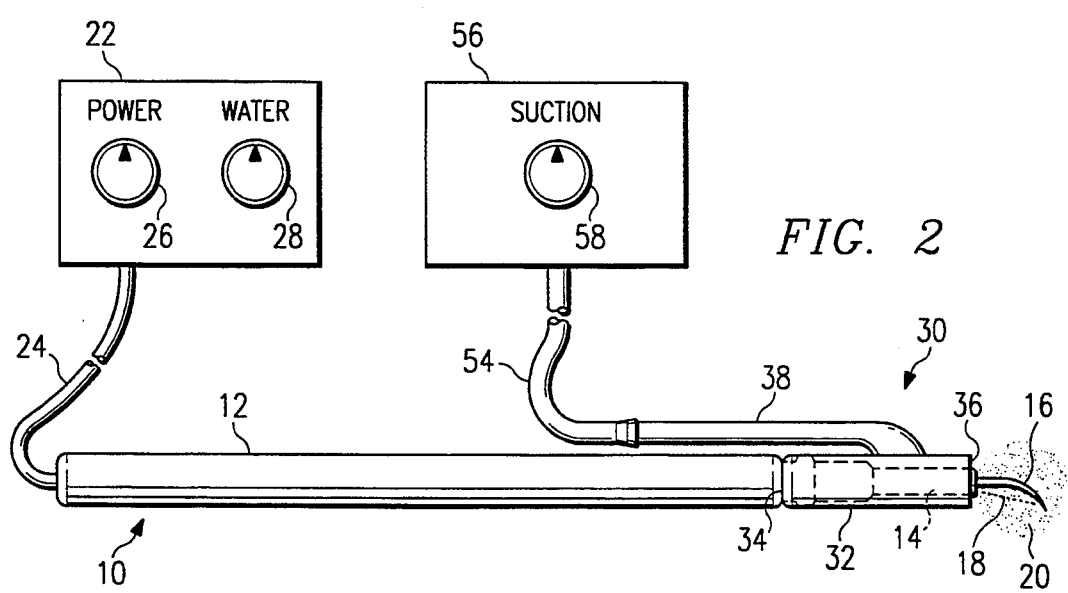
FIG. 2 illustrates the structural features of the suction hood assembly according to a presently preferred embodiment, as attached to an ultrasonic device.
Figure 3:
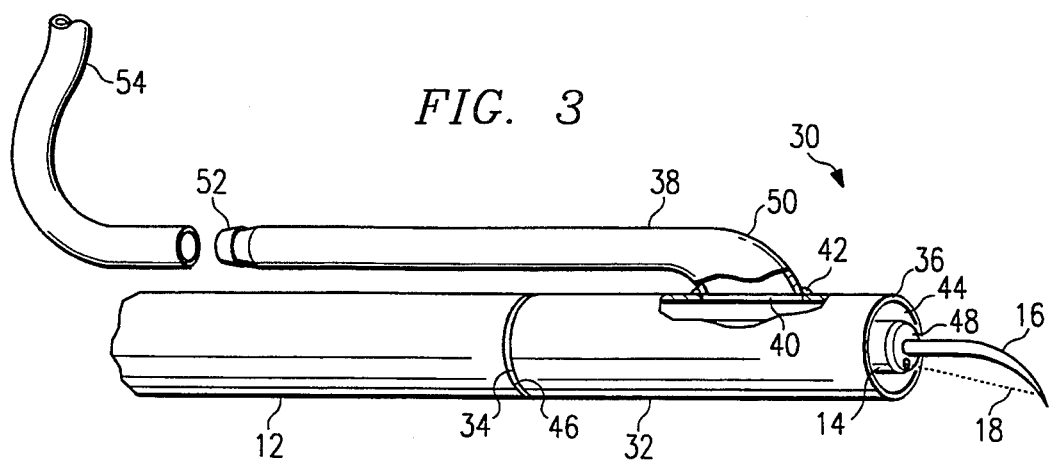
FIG. 3 illustrates an oblique end view of the suction hood assembly, illustrating the annulus thereof.

With reference now to FIGS. 2 and 3, there is illustrated a conventional ultrasonic handpiece assembly 10 equipped with a suction hood assembly 30, constructed according to the invention. It should be understood at the outset that the use of the invention is described in conjunction with an ultrasonic device, but the invention may find a variety of applications with many other medical and dental devices. The suction hood assembly 30 includes a cylindrical body 32, open at each end thereof. One end 34 of the cylindrical body 32 fits snugly around the handpiece 14 to prevent the passage of air, liquid or suction between the handpiece 12 and the cylindrical body 32. The outer end 36 of the cylindrical body 32 is open and radially spaced from the ultrasonic insert 14. This is shown more clearly in FIG. 3 of the drawings. A suction tube 38 is molded or fixed around an opening 40 formed in the sidewall of the cylindrical body 32. In this manner, when a suction is applied to the end of the tube 38, the suction draws in liquid, particles and mist via the outer, open end 36 of the cylindrical body 32. The engaging end 34 of the cylinder body 32 is fitted to the handpiece 12 in a manner that seals the cylindrical body 32 to the smooth-handled handpiece 12. Preferably, a friction fit is utilized to achieve a seal between the parts.

As shown in FIG. 3, when the suction tube 38 is constructed of metal, it can be soldered, brazed or welded, such as shown by 42, to the cylindrical body 32, which can also be constructed with metal, such as brass. As an alternative, the cylindrical body 32 and the suction tube 38 can be molded of plastic as an integral unit. It is contemplated that the suction hood assembly 30 can be economically molded with an ABS, or other suitable type of plastic.

With particular reference to FIG. 3, there is shown the annulus 44 defined by the radial spacing between the cylindrical body 32 and the ultrasonic insert 14. In the preferred embodiment of the invention, the radial distance therebetween is about 6.1 millimeters. The inside diameter of the cylindrical body 32 is about 14.3 millimeters, thereby providing an area of the annulus of about 147 square millimeters. It has been found by experimentation that a substantial annulus area is required to provide adequate control over the size of the aerosol envelope 20. It is believed that a large annulus operating with a high volume, low suction source is much preferable to a small area, high suction annulus. The available suction at medical and dental offices is generally about 35–40 cu. ft. per minute. In the preferred embodiment of the invention, the axial length of the cylinder body 32 is about 57.75 millimeters and thereby extends from the shoulder 46 of the ultrasonic handpiece 12 substantially to the end 48 of the insert 14. Preferably, the sidewall thickness of the cylindrical body 32 is uniform, although it need not be, and is contemplated to be about 0.60 millimeters thick. In practice, the end 48 of the insert 14 extends beyond the edge 36 of the cylindrical body 32 about 3 millimeters. The edge 36 of the cylinder body 32 is about 25–30 mm from the end of the tip 16. It has been found that this structural arrangement is very effective to provide an adequate influence of the suction in the annulus 44 to control the size of the aerosol envelope 20. By experimentation, it has been found that by varying the average available dental office suction flow with a gate valve, the size of the envelope can be varied from about 25.4 cm diameter to as about zero cm in diameter. By controlling the envelope to a size of about 2.54 cm, the aerosol envelope is contained within the mouth of the patient, and the transfer of particles and droplets is substantially reduced. In addition, by utilizing a smaller aerosol envelope 20, both the surgeon and the patient become less soaked. The reduced size of the aerosol envelope can be achieved without reducing the flow of water through the ultrasonic handpiece assembly 10, whereby the cooling properties are not comprised. Indeed, as will be described more fully below, by reducing the amount of hot water in the jet 18 that reaches the tip 16, the tip also operates at a reduced temperature.

Figure 4:
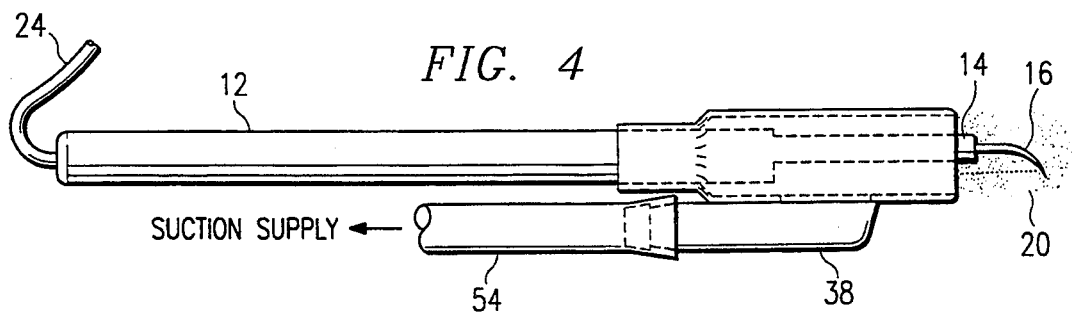
FIG. 4 illustrates another embodiment of the suction hood assembly according to the invention.
Figure 5:
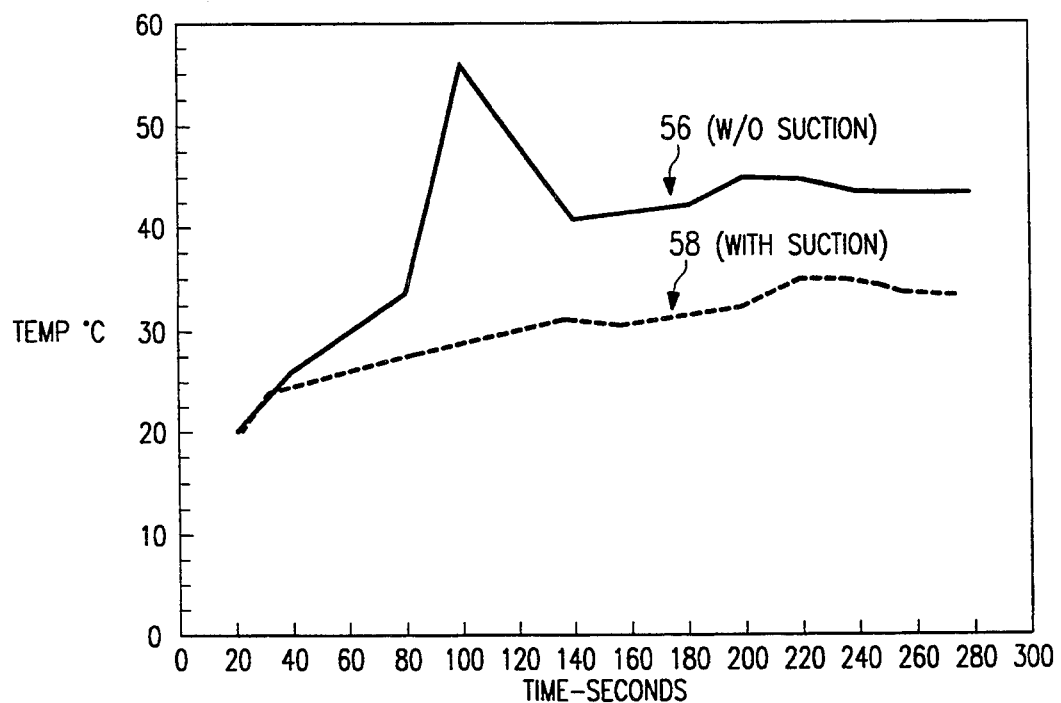
FIG. 5 graphically illustrates the ultrasonic tip temperature when the ultrasonic device is utilized with and without the invention.
Figure 6:
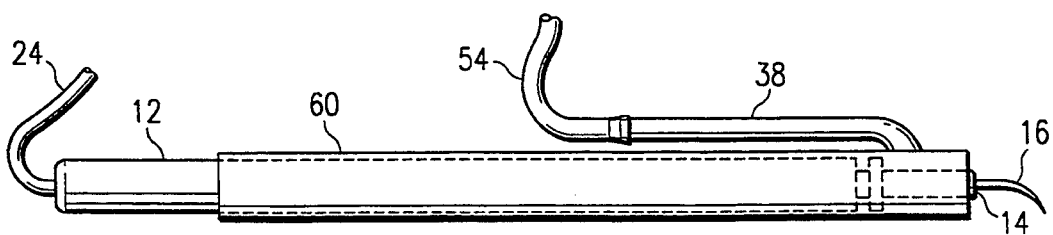
FIG. 6 shows another embodiment of the invention, in which the cylinder body is extended to cover a large portion of the handpiece.

A technical advantage realized by the invention is that the suction hood assembly 30 is easily removable from the handpiece assembly 10, thereby making both items easily cleaned and sterilized. In view that body fluids and matter are removed from the patient via the suction annulus 44, both the handpiece 10 and the suction hood 30 must be sterilized before reuse. It should be noted that in this embodiment, the external surface of a portion of the handpiece 12 usually becomes contaminated, and requires sterilization. A further advantage of the suction hood assembly 30 is that it can be easily manufactured at a low cost, and thus can be considered a disposable item. It is contemplated that the suction hood 30 can be injection molded with an ABS, or other type of plastic. The rigidity of the cylinder 32 prevents collapse of the body thereof when a suction or hand pressure is applied thereto. As is known, in order to effectively use the ultrasonic device, the surgeon must grip the device tightly. This contrasts with the pliable sleeve shown in the Eaton patent identified above. Further, the frontal end 36 of the cylinder body 32 can be formed with a diameter different than that of the back end 34 to achieve a desired area of the annulus 44, as well as accommodate different sizes of handpieces 10. This aspect is shown in FIG. 4.

While the body 32 of the suction device 30 (FIG. 3) is shown having a circular cross section, the cross section at the back 34 of the body can be of any shape corresponding to the shape of the handpiece 12 onto which it is to be secured. By providing a tight and snug fit between the back end 34 of the cylindrical body 32 with the ultrasonic handpiece 12, the parts can be sealed together. In some instances, it may be advantageous to utilize one or more O-rings situated between the inner sidewall of the cylindrical body 32 and the outer surface of the ultrasonic handpiece 12. Either handpiece 12 or the insert 14 may be modified or manufactured with one or more annular grooves in the outer surface thereof to accommodate the O-rings, over which the suction hood assembly 30 is inserted and sealed thereto. Alternatively, internal annular grooves can be formed within the cylindrical body 32 to accommodate the O-rings, again for sealing to the outer surface of the ultrasonic handpiece 12. As noted above, the frontal end 36 of the cylindrical body 32 can be formed with a desired diameter to achieve a desired area of the annulus 44, thereby to achieve particular suction characteristics for influencing the nature and size of the aerosol envelope 20. In other words, the frontal end 36 of the cylindrical body need not be circular, but can be oval, rectangular, etc. Also, while the edge of the frontal end 36 of the cylindrical body 32 is shown cut or formed at a right angle with respect to the longitudinal axis of the hood, such aspect is not necessary. Indeed, the frontal edge 36 can be formed at an angle and aligned with respect to the ultrasonic tip 16 to facilitate using the unit in a patient's mouth or body cavity.

The opening 40 is preferably formed in the sidewall of the cylindrical body 32, midway between the frontal end 36 and the back end 34. The suction tube 38 includes an angle 50 so that the elongate portion of the tube 38 extends backwardly adjacent to the ultrasonic handpiece 12 to thereby make the unit compact and easily used within small places, such as in the mouth of a patient. Preferably, the elongate portion of the suction tube 38 is about 175–200 millimeters in length, with an end having an annular ridge 52 for securement of plastic tubing, or the like, thereto. A C-clip can be utilized to clip the suction tube 38 to the handpiece 12 to prevent inadvertent disengagement of the suction hood assembly 30 from the ultrasonic assembly 10.

With reference back to FIG. 2, the suction tube 38 of the hood assembly 30 is shown connected to a conventional source 56 of suction or vacuum, or to a central evacuation system. The source of suction is characterized by a relatively small suction and a large volume. The source of suction 56 includes a manual control 58 for controlling the amount of suction applied to the suction hood assembly 30. As noted above, by utilizing the suction hood assembly 30, the size of the aerosol envelope 20 is controlled, and in addition, a substantial amount of water jetted directly from the ultrasonic assembly 10 can be recovered, thereby minimizing much of the need for an auxiliary suction tube located in the patient's mouth. The suction hood assembly recovers about 85%–95% of the hot water from the jet 18, the remaining portion reaches the ultrasonic tip 16. Less hot water spray is thus discharged in the patient's mouth. As a consequence, the patient feels more comfortable, and requires less spitting or expelling of fluids, and a reduced tendency to swallow due to the aerosol and spray hitting the patient's throat. The suction source 56 is shown having a manual control 58, however, those skilled in the art may find it advantageous to form a finger-operated suction valve or control integral in the suction tube 38. In this manner, the surgeon may conveniently vary the amount of suction with, for example, a pressure responsive valve, to vary the amount of suction and thus the size of the aerosol envelope 20. With this arrangement, the surgeon may temporarily interrupt the suction to flood or wash the area of concern with water.

With reference now to FIG. 5, there is illustrated a comparison of the temperature of the ultrasonic tip 16 with the use of the suction hood assembly 30, and without such assembly. Particularly, solid line 56 of the graph shows the use of the ultrasonic handpiece assembly 10 without the suction hood assembly 30, while broken line 58 illustrates the temperature of the ultrasonic tip 16 when influenced by the suction of the hood assembly 30. The temperature data of FIG. 5 was taken by measuring the temperature (over a period of time) of an experimental brass tooth, as the thermal energy was transferred from the ultrasonic tip 16, under conditions in which the hood assembly was first utilized, and then later not utilized. As can be seen, there is an initial period of time in which the tip 16 becomes uncomfortably hot, when the suction hood assembly 30 is not utilized. This temperature peak is much less pronounced when using the suction hood assembly 30. As can also be appreciated from FIG. 5, the long-term use of the ultrasonic handpiece assembly 10 with the invention results in reduced operating tip temperature, by as much as 10° Celsius. In practice, the ultrasonic tip temperature operated without the influence of a suction reaches a steady state of about 128°–132° F. When operated with the suction hood assembly, the tip temperature is reduced to about 112°–114° F. Because the tip 16 of the ultrasonic insert 14 operates at a reduced temperature, the patient's teeth, bone, etc. are not heated as much, thereby making the experience of the patient less traumatic.

FIG. 6 illustrates another embodiment of the invention, wherein the cylindrical body 60 is elongated and extends along a substantial length of the ultrasonic handpiece 12. While not shown, the elongate cylindrical body 60 may have formed on the inner cylindrical sidewall an annular ridge that engages the outer surface of the handpiece 12 to form a seal. Optionally, an O-ring or other suitable seal can provide a seal between the parts. With this embodiment, the surgeon generally grasps the elongate cylindrical body 60, rather than the ultrasonic handpiece 12. When the elongate body 60 is formed of plastic, the transfer of heat from the ultrasonic handpiece 12 to the elongate hood 60 is reduced, thereby resulting in a unit that is cooler to handle by the surgeon. In this embodiment, the elongate body is friction fit to the ultrasonic handpiece, and thus is sealingly engaged thereto. The elongate hood 60 can be separated from the handpiece and can be sterilized in an autoclave, or otherwise disposed of, while the handpiece can be cleaned in a conventional manner.

From the principles and concepts of the invention set forth above, those skilled in the art can readily appreciate that the suction hood assembly can also be manufactured as part of the ultrasonic handpiece assembly 10.

Indeed, the suction hood assembly can be formed integral with the handpiece, or as part of the insert. Although the disposability of the suction hood is then limited, the other qualities and advantages can yet be realized.

Figure 7:
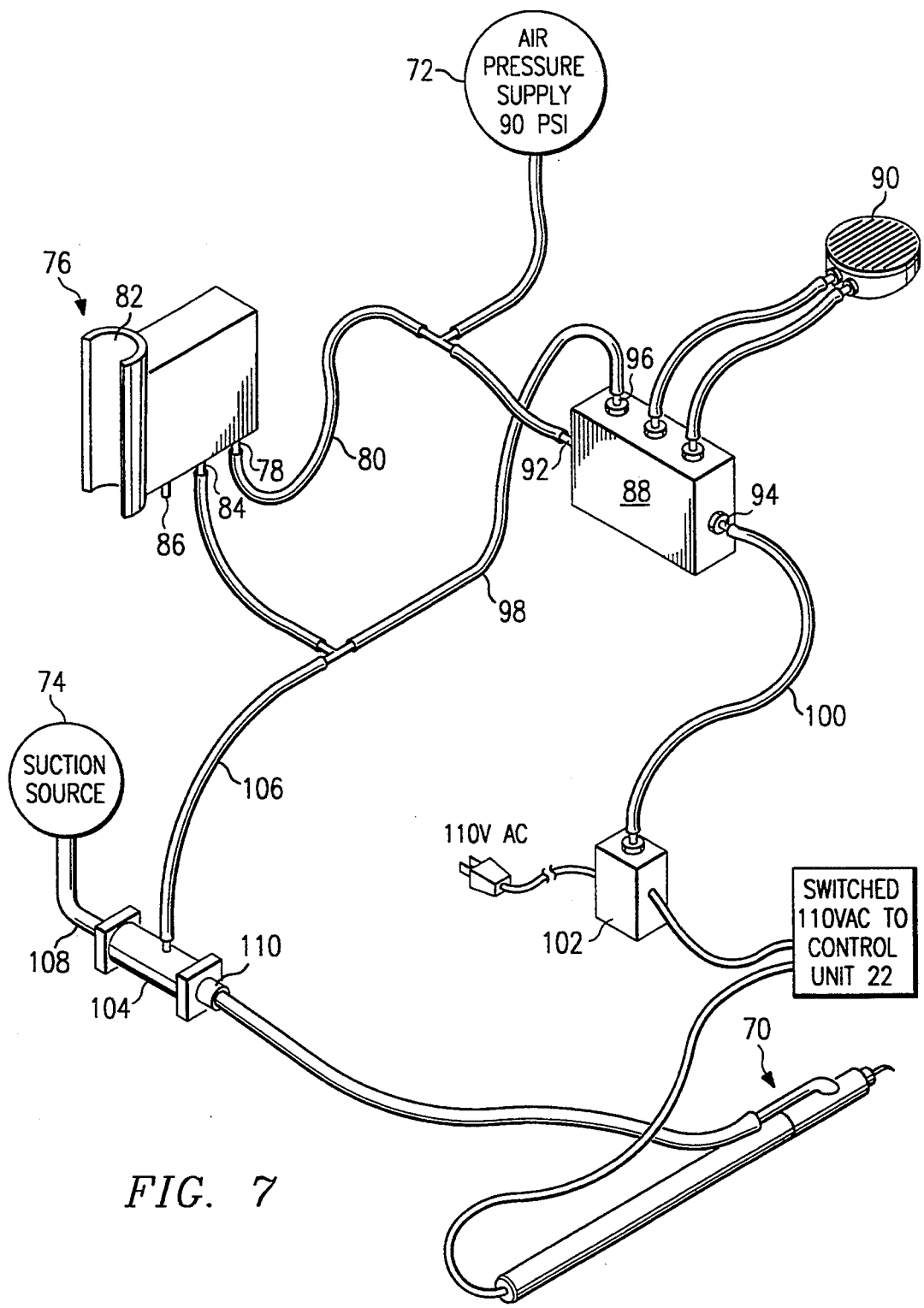
FIG. 7 illustrates a control system for controlling the application of suction and AC power to the ultrasonic device of the invention.

FIG. 7 illustrates an air pressure/suction system for driving the ultrasonic device 70 of the invention. The system includes a source 72 of air pressure and a source 74 of suction. The source 72 of air pressure is connected to a number of valves and switches to control the operation of the ultrasonic device 70, depending upon the actions of the surgeon. The source 74 of suction is utilized to control the size of the aerosol envelope and to remove fluids from the area of operation.

In the preferred embodiment of the invention, the air pressure supply 72 is connected to a device holder 76 which controls activation of the ultrasonic device 70, depending upon whether or not the device 70 has been placed within the holder 76, or removed therefrom. The air pressure supply 72 is connected to an inlet 78 by way of a tube 80. While not shown, the device holder 76 includes an actuation button or arm which senses when the ultrasonic device has been placed in the cradle 82 of the holder 76. The actuation arm of the holder 76 causes the air pressure coupled to the inlet 78 to be switched internally through a valve to an outlet 84. On the other hand, an air release port 86 on the device holder 76 allows air pressure existing at the outlet port 84 to be exhausted to the air when the internal switch is closed, i.e., when the ultrasonic device 70 has been removed from the holder 76. The device holder 76 is of conventional construction, obtainable from American Dental Accessories, Inc., as Model #10-03.

The air pressure supply 72 is also coupled directly to a selector block 88, which is commercially available from the above referenced supplier, as Model #49-86. Connected to the selector block 88 is a foot-operated switch 90 which, when operated, allows air pressure at the inlet 92 of the selector block to be coupled to an outlet 94 thereof. In addition to the actuation of the foot-operated switch 90, the selector block 88 requires the absence of air pressure at a pilot input 96. The pressure supplied to the pilot input 96 of the selector block 88 is from a tube 98 connected to the pressure outlet 84 of the device holder 76. Hence, air pressure is available at the outlet 94 of the selector block 88 only when the foot-operated switch 90 is actuated and when the ultrasonic device 70 has been removed from the device holder 76. The outlet 94 of the selector block 88 is coupled by tubing 100 to a pressure-operated electrical switch 102 which controls electrical current to the control unit 22 of the ultrasonic device. In other words, when air pressure is coupled from the selector block 88 to the switch 102, 110 volt AC power is connected to the ultrasonic control unit 22.

An in-line suction valve 104 is connected by tubing 106 to the outlet 84 of the device holder 76. The suction valve 104 is of the normally open type, in which the inlet 108 is connected through to the outlet 110 in the absence of air pressure supplied to the tube 106. The suction valve 104 is of the conventional type that has an inflatable stopper that inflates and closes the valve in the presence of air pressure in tube 106, and causes the passage therethrough to be open in the absence of air pressure. The valve 104 is obtainable from the above-referenced supplier as Model #30-75.

In operation of the system shown in FIG. 7, when the ultrasonic device 70 has been placed in the device holder 76, the internal valve of the holder is open and thus there is air pressure coupled to the outlet tubing 98 and 106. With a source of air pressure applied to the selector block 88 from pilot input 96, the actuation of the foot-operated switch 90 is ineffective to operate the electrical switch 102. Thus, the electrical power from control unit 22 to the ultrasonic device 70 is removed. Also, and importantly, the suction valve 104 is closed and thus suction to the suction hood of the ultrasonic device 70 is interrupted. The removal of the suction source 74 from the ultrasonic device 70 eliminates the annoying suction noise.

When the ultrasonic device 70 is removed from the device holder 76 by the surgeon, the entire system is activated and made ready for use. In other words, the device holder 76 prevents air pressure from being coupled therethrough to the tubing 98 and 106, whereby the suction valve 104 is opened and suction is coupled to the ultrasonic device 70. Any air pressure in the outlet tubing 98 and 106 is relieved or exhausted through the exhaust port 86 of the device holder 76. Further, with no air pressure available at the pilot input 96 of the selector block 88, air pressure from the supply 72 can be coupled to the switch 102, depending upon whether or not the surgeon has activated the foot-operated switch 90. In this condition, when the foot-operated switch 90 is depressed, the switch 102 is activated, whereby 110 volt electrical power is coupled to the control unit 22 of the ultrasonic device 70. The system of FIG. 7 is constructed of conventional components, but interconnected in such a manner as to provide the advantages noted above.

From the foregoing, the suction hood assembly of the invention has been described and the numerous advantages attained thereby. The suction hood assembly can be easily manufactured as a low cost item, thereby making it disposable. The invention, in certain embodiments thereof, is removable from the ultrasonic handpiece, and thus easily cleaned or sterilized. Importantly, because of its construction, and utilization with ultrasonic handpieces, the suction generated in the vicinity of the ultrasonic tip recovers the water spray and the mist, thereby controlling the size of the aerosol envelope. In doing so, the invention substantially reduces the transfer of microdroplets of body fluids from the patient to the surgeon. By recovering a portion of the water spray jetted toward the ultrasonic tip, which water spray has absorbed heat from the ultrasonic pile, the tip operates at a reduced temperature. The water flow through the ultrasonic handpiece need not be reduced, however, whereby the cooling of the handpiece is not compromised.

While the preferred and other embodiments of the methods and apparatus have been disclosed with reference to specific structures, techniques and the like, it is to be understood that many changes in detail may be made as a mater of engineering choices without departing from the spirit and scope of the invention as defined by the appended claims. Indeed, those skilled in the art may prefer to embody the apparatus in other forms, and in light of the present description, they will find it easy to implement that choice. Also, it is not necessary to adopt all of the various advantageous features of the present disclosure into a single composition assembly in order to realize the individual advantages disclosed herein.

What is claimed is:

1. An aerosol recovery assembly for use with an ultrasonic device of the type having an elongate handpiece, a tip, and an orifice through which water spray is jetted toward the tip and generates an aerosol, the combination of said aerosol recovery assembly and a portion of said ultrasonic device comprising:
   a source of suction;
   an insert of said ultrasonic device;
   a rigid cylinder body insertable on at least a portion of the handpiece, said cylinder body having opposing first and second open ends, said first end being radially spaced from the insert to define an annulus, one end of which is open, said second end fitting securely to the handpiece for supporting and sealing the cylinder body to the ultrasonic device;
   a suction tube attached to a sidewall of the cylinder body and sealed around an opening in the sidewall so that when the source of suction is connected to the suction tube, at least a portion of the aerosol is drawn in via the annulus between the ultrasonic insert and the cylinder body and extracted via the suction tube; and
   the annulus and a suction path between the open end of the annulus and the suction source being of sufficient area to transfer a volume of air to the suction source such that an envelope of the aerosol surrounding the tip of the ultrasonic device can be controlled and reduced down to a diameter of at least about 2.54 cm, as a function of the amount of suction applied to the suction tube.

2. The aerosol recovery assembly of claim 1, wherein the first end of the cylinder body has a different diameter than said second end.

3. The aerosol recovery assembly of claim 1, wherein said cylinder body has a length so that the second end thereof engages the handpiece and the first end is spaced from the end of the insert about 3 millimeters.

4. The aerosol recovery assembly of claim 1, wherein said assembly is constructed of a rigid plastic and is removably attachable to the ultrasonic device and is thus disposable.

5. The aerosol recovery assembly of claim 1, wherein the source of suction is adjustable between 15-60 cu. ft/min.

6. The aerosol recovery assembly of claim 1, further including in combination the ultrasonic device.

7. The aerosol recovery assembly of claim 1, wherein the annulus area is between 17.4 and 96.0 square millimeters.

8. The aerosol recovery assembly of claim 1, wherein the suction source is connectable to said rigid cylinder body to provide a suction in said annulus to control the size of an aerosol envelope generated by the ultrasonic device.

9. The aerosol recovery assembly of claim 8, wherein said suction source is adapted to produce a suction in the annulus for recovering a portion of the water spray jetted toward the ultrasonic tip before said portion of water spray reaches the tip, thereby reducing the operating temperature of the tip.

10. The aerosol recovery assembly of claim 8, wherein said cylinder body is elongate and extends over a substantial portion of the ultrasonic handpiece.

11. The aerosol recovery assembly of claim 1, wherein the cylinder body is sealed to the ultrasonic handpiece by a friction fit.

12. The aerosol recovery assembly of claim 1, wherein the cylinder body is sealed to the ultrasonic handpiece with an elastomeric sealing ring.

13. The aerosol recovery assembly of claim 1, further including a control for varying the amount of suction in said annulus to thereby control the size of an envelope of said aerosol.

14. An aerosol containment and recovery assembly for use with an ultrasonic device, said combination comprising:
   an ultrasonic scaler, including:
      a handpiece,
         an elongated insert inserted into an open end of the handpiece, said insert having an orifice through which water is jetted toward a tip;
   the aerosol containment and recovery assembly including,
      a rigid suction hood adapted for enveloping at least a portion of the ultrasonic insert to form an annular space therebetween at a frontal end of the suction hood, and engageable with the ultrasonic handpiece for sealing to the handpiece to support the suction hood to the ultrasonic scaler and to prevent entrainment of air into the annular space at a back end of the suction hood, said annular space being of an area between about 17 $mm^2$ to about 147 $mm^2$ to provide transfer of an effective volume of air to contain and recover an aerosol generated by the jetted water, and said frontal end being spaced sufficiently from an end of the ultrasonic tip for allowing working thereof with tissue without interference by the suction hood and for allowing substantial air and particulate matter to be sucked into the annular space; and
      a suction tube fixed to a sidewall of the suction hood, about an opening in the sidewall so that a suction channel is formed in the annular space between the suction hood and the insert, the opening in the sidewall of the suction hood being of sufficient area to allow a sufficient volume of air to pass therethrough to contain and control the size of the aerosol generated.

15. The combination of claim 14, wherein said suction hood is formed integral with said ultrasonic device.

16. The combination of claim 14, wherein an open end of said suction hood terminates adjacent a base of said ultrasonic tip so as to recover a portion of aerosol generated by the tip.

17. The combination of claim 14, wherein the aerosol recovery assembly is removable from the ultrasonic scaler, and is friction fittable with the ultrasonic handpiece when attached thereto.

18. A method of controlling an aerosol envelope generated by an ultrasonic device of the type having a water jet directed toward an ultrasonic operated tip, comprising the steps of:
   developing a suction annularly around a base of the ultrasonic tip so as to influence aerosol mist generated by the tip;
   recovering a portion of the aerosol mist generated by the ultrasonic tip so that only a small aerosol envelope is developed around the ultrasonic tip; and
   controlling the size of the aerosol envelope by controlling the amount of suction developed in an annular area adjacent the base of the ultrasonic tip.

19. The method of claim 18, further including recovering a portion of the water from the jet before the water is converted into an aerosol by the tip, thereby allowing the tip to operate at a lower temperature.

20. The method of claim 18, further including developing an annular area of suction by surrounding at least a portion of an ultrasonic insert with a rigid cylinder, sealing the cylinder to an ultrasonic handpiece, and removing the recovered aerosol from the annular area.

21. The method of claim 18, further including reducing the size of the aerosol envelope down to a diameter of at least about 2.54 cm.

22. The method of claim 18, further including recovering the aerosol mist in an annular area between the ultrasonic device and a cylinder body surrounding the ultrasonic device, with the annular area being between about 17 $mm^2$ and about 147 $mm^2$.

23. The method of claim 18, further including using the ultrasonic device in dental operations.

24. In an ultrasonic device of the type having an ultrasonic operated tip that generates an aerosol mist, a method for influencing the aerosol mist and for cooling the ultrasonic device, comprising the steps of:
generating an area of suction to influence the aerosol mist;
drawing the aerosol mist by use of the area of suction into an area adjacent at least a portion of the ultrasonic device; and
cooling the ultrasonic device by the action of the aerosol mist being drawn by the suction.

25. The method of claim 24, further including drawing the aerosol mist into an annulus surrounding at least a frontal portion of the ultrasonic device for cooling thereof.

26. The method of claim 24, further including drawing the aerosol mist into an annulus surrounding a majority of a handle portion of the ultrasonic device for cooling thereof.

27. The method of claim 26, further including forming the area of suction between a cylindrical hood surrounding at least a portion of the ultrasonic device and connecting the area of suction to a source of suction.

28. The method of claim 27, further including cooling the cylindrical hood by the action of the aerosol mist, and conducting heat from the ultrasonic device to the cylindrical hood.

29. An aerosol recovery assembly for use with an ultrasonic device of the type having an elongate handpiece, an insert, a tip, and an orifice through which water spray is coupled to the tip to generate an aerosol, comprising in combination:
an insert of said ultrasonic device;
a rigid cylinder body insertable on at least a portion of the handpiece, said cylinder body being uniform in diameter and having opposing first and second open ends, said first end being radially spaced from the insert to define an annulus, said second end fitting securely to the handpiece for supporting and sealing the cylinder body to the ultrasonic device;
a suction tube attached to a sidewall of the cylinder body and sealed around an opening in the sidewall so that when a source of suction is connected to the suction tube, at least a portion of the aerosol is drawn in via the annulus between the ultrasonic insert and the cylinder body and extracted via the suction tube; and
the annulus being of sufficient area such that an envelope of the aerosol surrounding the tip of the ultrasonic device can be controlled as to size as a function of the amount of suction applied to the suction tube.

30. An aerosol recovery assembly for use with an ultrasonic device of the type having an elongate handpiece, an insert, a tip, and an orifice through which water spray is coupled to the tip to generate an aerosol, comprising in combination:
an insert of said ultrasonic device;
a holder for holding the ultrasonic device, said holder having a valve responsive to the placement of the ultrasonic device in said holder to remove the source of suction from the aerosol recovery assembly;
a rigid cylinder body insertable on at least a portion of the handpiece, said cylinder body having opposing first and second open ends, said first end being radially spaced from the insert to define an annulus, said second end fitting securely to the handpiece for supporting and sealing the cylinder body to the ultrasonic device;
a suction tube attached to a sidewall of the cylinder body and sealed around an opening in the sidewall so that when a source of suction is connected to the suction tube, at least a portion of the aerosol is drawn in via the annulus between the ultrasonic insert and the cylinder body and extracted via the suction tube; and
the annulus being of sufficient area such that an envelope of the aerosol surrounding the tip of the ultrasonic device can be controlled as to size as a function of the amount of suction applied to the suction tube.

31. The aerosol recovery assembly of claim 30, further including a selector block responsive to the actuation of the holder by removal of the ultrasonic device therefrom to allow electrical power to be coupled to the ultrasonic device.

32. The aerosol recovery assembly of claim 31, further including a source of air pressure coupled to the selector block and being switchable by the selector block for activating a switch to couple electrical power to the ultrasonic device.

* * * * *